US010036716B2

(12) United States Patent
Uetaki et al.

(10) Patent No.: US 10,036,716 B2
(45) Date of Patent: Jul. 31, 2018

(54) SOLAR POWER PANEL FAILURE DETECTION AND SEARCHING SYSTEM

(71) Applicant: SKYROBOT INC., Kanagawa (JP)

(72) Inventors: Ryohei Uetaki, Tokyo (JP); Daisuke Kaio, Kanagawa (JP)

(73) Assignee: SKYROBOT INC., Tokyo (JP)

( * ) Notice: Subject to any disclaimer, the term of this patent is extended or adjusted under 35 U.S.C. 154(b) by 115 days.

(21) Appl. No.: 15/305,063

(22) PCT Filed: Apr. 22, 2014

(86) PCT No.: PCT/JP2014/002262
§ 371 (c)(1),
(2) Date: Nov. 26, 2016

(87) PCT Pub. No.: WO2015/162637
PCT Pub. Date: Oct. 29, 2015

(65) Prior Publication Data
US 2017/0184524 A1    Jun. 29, 2017

(51) Int. Cl.
*H04N 7/18* (2006.01)
*G01N 25/72* (2006.01)
(Continued)

(52) U.S. Cl.
CPC ........... *G01N 25/72* (2013.01); *B64C 39/024* (2013.01); *B64D 17/80* (2013.01); *B64D 45/00* (2013.01); *B64D 47/08* (2013.01); *G01J 5/0066* (2013.01); *G01J 5/047* (2013.01); *G05D 1/10* (2013.01); *G06K 9/0063* (2013.01); *H02S 50/10* (2014.12); *H04N 5/33* (2013.01);
(Continued)

(58) Field of Classification Search
CPC ........ G01N 25/72; H02S 50/10; B64C 39/024

USPC .......................................................... 348/144
See application file for complete search history.

(56) References Cited

U.S. PATENT DOCUMENTS 6,868,314 B1 * 3/2005 Frink ........................ B64C 1/00
                                                              244/119
2012/0242321 A1   9/2012 Kasai et al.
2013/0200207 A1 * 8/2013 Pongratz ............... B64C 39/024
                                                                244/2

FOREIGN PATENT DOCUMENTS

JP            6-137823 A        5/1994
JP         2003-110981 A        4/2003
(Continued)

OTHER PUBLICATIONS

"How to get a true picture of faulty solar panels," DEMM Engineering & Manufacturing, Dec. 2013, p. 28, http://digital.adrenalin.co.nz/i/220740.

*Primary Examiner* — Thai Tran
*Assistant Examiner* — Jose Mesa
(74) *Attorney, Agent, or Firm* — Im IP Law; C. Andrew Im

(57) ABSTRACT

A solar power panel failure search and detect system to search and detect malfunctioning or failed sites of a solar power panel. A search unit is installed in a remotely controllable aerial vehicle. The search unit maintains a constant distance between a solar panel and a failure detector, and maintains the failure detector at an optimum angle. A control unit controls a flight path and a flight angle of the aerial vehicle and controls/regulates an angle of the failure detector, a receiver, a processor, and the search unit. The search unit has an angle sensor, the failure detector, an angle adjuster and an imaging device. The control unit has a transmitter to transmit the search result data.

7 Claims, 1 Drawing Sheet

(51) Int. Cl.
  *G01J 5/00* (2006.01)
  *G01J 5/04* (2006.01)
  *H04N 5/33* (2006.01)
  *G06K 9/00* (2006.01)
  *B64C 39/02* (2006.01)
  *B64D 47/08* (2006.01)
  *B64D 17/80* (2006.01)
  *B64D 45/00* (2006.01)
  *G05D 1/10* (2006.01)
  *H02S 50/10* (2014.01)

(52) U.S. Cl.
  CPC .... *B64C 2201/146* (2013.01); *B64D 2201/00* (2013.01); *G01J 2005/0077* (2013.01)

(56) References Cited

FOREIGN PATENT DOCUMENTS

| | | |
|---|---|---|
| JP | 2006-82775 A | 3/2006 |
| JP | 2011-146472 A | 7/2011 |
| JP | 2011-149839 A | 8/2011 |
| JP | 2012-81936 A | 4/2012 |
| JP | 2012-145346 A | 8/2012 |
| JP | 2012-205061 A | 10/2012 |

* cited by examiner

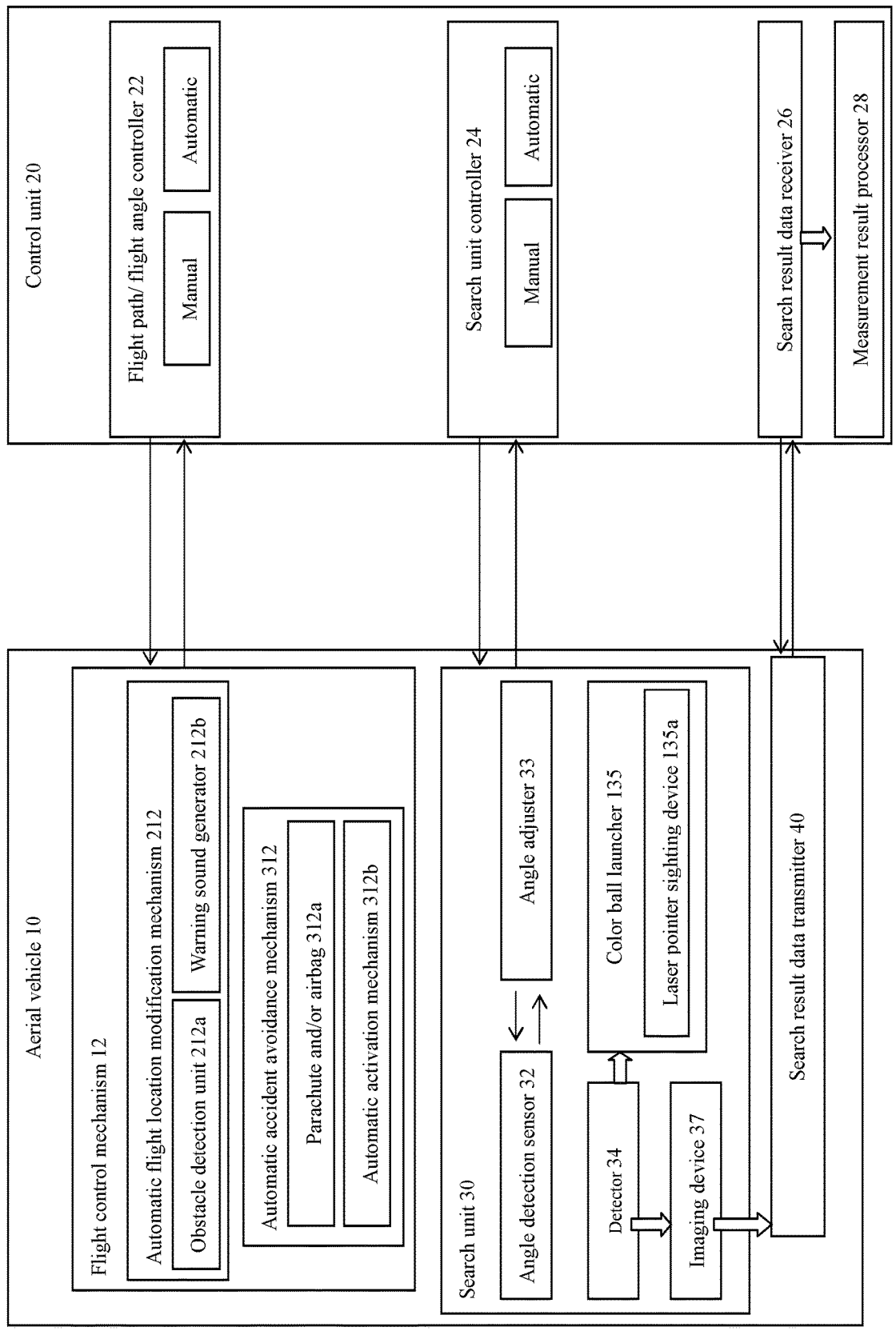

SOLAR POWER PANEL FAILURE DETECTION AND SEARCHING SYSTEM

RELATED APPLICATIONS

This application is a § 371 application from PCT/JP2014/002262 filed Apr. 22, 2014, which is herein incorporated by reference in its entirety.

TECHNICAL FIELD

The present invention relates to a search system for detecting malfunction and/or failure sites in a solar power panel, more particularly relates to an aerial vehicle-based search system for detecting anomaly sites from above using aerial photography and/or ultrasonic examination equipment or the like, and still more particularly relates to a solar panel failure search and detect system capable of detecting solar panel malfunction and/or failure sites from an optimum location by using a ground-based control unit to control flight path and flight angle of an aerial vehicle to maintain constant distance/angle between an ultrasonic and/or laser beam emitted from an aerial vehicle-mounted search unit and a module surface and/or cell surface of the solar power panel.

BACKGROUND OF THE INVENTION

The solar power panel, which is an electric power generator that uses the photovoltaic effect to convert solar energy directly into electric power, has attracted attention as an electric power source using renewable energy to generate power steadily from natural energy and has been adopted in a broad range of industrial sectors. Conversion efficiency improvements and production cost reductions have led to wide utilization, that now extends even to ordinary homes, while a concomitant rise in maintenance requirements has led to the development of various detection systems going beyond visual inspection that include, inter alia, ones employing stationary equipment-based methods, as well as ones that detect failure sites using aerial photography.

The solar power panel is an assembly of multiple modules and/or cells, namely, of multiple electrically interconnected modules and/or cells. As a solar power panel exhibits a phenomenon of conversion efficiency decline in proportion as temperature of the modules and/or cells increases, a problem of conversion efficiency degradation arises even when no failure of the power generation or power storage has occurred. In light of this, malfunction detection systems and the like have been developed for performing repair that use thermographic cameras to detect not only heating owing to module and/or cell failure or similar but also module and/or cell temperature increase owing to, for instance, heating caused by aging degradation or the like.

Conventional failure site detection methods use detectors installed array-by-array of series-connected module strings or parallel-connected strings to perform malfunction detection by monitoring power generation condition, but they need considerable labor and time to detect which cell of which module failed. A variety of systems have therefore been developed including, inter alia, ones that involve an inspector carrying a thermographic camera or other measuring instrument to the installation and directly photographing the solar power panel, ones that periodically detect surface temperature anomalies with a thermographic camera or the like installed at a fixed observation point, and attachment type ones that detect malfunction at a fixed angle by utilizing mechanical control to slide a thermographic camera or other mechanically controlled detector at fixed intervals defined on a surface.

Solar panels of industrially applicable scale need to be of at least a certain size, and since use of sunlight is necessary, the prevailing situation is that installation sites are generally expansive and located in places where inspection is difficult. With the aforesaid conventional search/detect systems using a manual or fixed thermographic camera or the like, problems are encountered during search and detection of it being impossible to maintain the thermographic camera or other detection instrument at an optimum angle and fixed distance with respect to the solar panel. On the other hand, in the attachment type system, although a fixed angle and distance can be maintained against the solar power panel, inconveniences arise in that detection instruments must be installed prior to search/detect and that equipment installation is costly and time consuming when the solar power panel is large scale.

Further, solar power panels are constituted of multiple identically shaped modules (or cells) electrically and continuously interconnected, so that when a malfunction is discovered from detection data from a large-scale solar power panel, a problem arises of much time being required to precisely pinpoint the location of the failed module (or cell) during later part replacement work carried out on an individual module (or cell) basis.

Development has therefore been desired of a search system for detecting solar power panel failure that does not require deployment of many workers or provision of a search unit on the solar power panel at the installation site, that can constantly maintain a fixed distance between a search unit and the solar panel, that can continuously maintain an optimum fixed angle between an ultrasonic or laser beam emitted by the search unit and the solar panel, and that enables accurate and suitable pinpointing of a detected malfunction or failure site instantaneously during replacement work.

Patent document 1: JP2012-205061A

OBJECT AND SUMMARY OF THE INVENTION

Problems to be Overcome by the Invention

The present invention has as an object to overcome the issues set out in the foregoing by providing a solar power panel failure search and detect system comprising a search unit installed in a remotely controllable aerial vehicle, which solar panel failure search and detect system operates a ground control unit to glide or hover an aerial vehicle equipped with a flight control mechanism, uses an aerial vehicle angle control mechanism together with a camera and an angle sensor of the search unit installed in the controllable aerial vehicle to constantly maintain a fixed distance between a solar panel and detection means and constantly maintain optimum failure detection means angle, and additionally comprises marking means for pinpointing a discovered malfunction site.

The solar power panel failure search and detect system according to the present invention for achieving the aforesaid object, which is a solar power panel search system that performs detection of malfunction or failure sites of a solar power panel using a search unit installed in a remotely controllable aerial vehicle, comprises:

an aerial vehicle equipped with an on-board search unit and a flight control mechanism for effecting aerial gliding and/or hovering flight by remote control;

a ground-based control unit equipped with control means for controlling aerial vehicle course and flight angle, means for controlling/regulating angle of detection means installed in the aerial vehicle, receiver means for receiving search result data, and analysis means for analytically processing measurement results;

a search unit equipped with an angle sensor for detecting angle between a module surface and/or cell surface of a solar power panel and the detection means, adjustment means for varying angle of the detection means and/or the aerial vehicle to maintain the detection means at a fixed angle to the module surface and/or cell surface of the solar power panel during search, detection means for measuring/detecting heat amount of the module and/or cell of the solar power panel, and imaging means including a camera for imaging solar power panel condition; and transmission means for transmitting search result data including measurement/detection values and image data to the ground control unit.

In a further configuration, the search unit measures/detects heat generation amount of modules and/or cells constituting the solar power panel individually using an ultrasonic and/or laser beam.

In a further configuration, the search unit performs a search while maintaining optimum search condition by using an ultrasonic and/or laser beam to measure distance to a module surface and/or cell surface of a solar power panel and measure angle to the module surface and/or cell surface of the solar power panel.

In a further configuration, the camera is configured as a thermographic camera.

In a further configuration, in order to pinpoint location of a malfunctioning or failed module and/or cell incorporated in a solar power panel, the search unit is equipped with a launcher for target irradiating a spot concerned with a laser pointer based on analysis results of the control unit and shooting a color marking ball.

In a further configuration, the aerial vehicle is equipped with an obstacle detector that comprises ultrasonic sensors and/or lasers at multiple locations and, upon approaching an obstacle (solar power panel included) closer than a certain distance, produces a warning sound and automatically modifies flight location.

In a further configuration, in order to protect the solar power panel and the aerial vehicle from a crash impact owing to failure or the like of the flight control mechanism, the aerial vehicle is equipped with an automatic accident avoidance mechanism for automatically activating/deploying an emergency parachute and/or airbag when an unflyable situation arises.

Effects of the Invention

Being configured in the manner described in detail in the foregoing, the solar power panel failure search and detect system according to the present invention offers the following effects.

1. The remote flight control mechanism of the aerial vehicle can maintain a fixed distance between the aerial vehicle and the solar power panel irrespective of the scale and installation topography of the solar power panel, the flight angle control means and the angle sensor of the detection means installed in the aerial vehicle enable measurement/detection with the detection means maintained at a fixed angle to the solar panel, and the transmission means can transmit search result data to the ground-based control unit.

2. Heat generation amount of solar panel modules (or cells) can be measured/detected individually using the ultrasonic and/or laser beam emitted by the detection means installed in the search unit.

3. By using the ultrasonic and/or laser beam sensor of the detection means installed in the search unit to measure distance or angle to the solar power panel, accurate measurement at a substantially perpendicular angle is possible and the flight path and angle of the aerial vehicle can also be controlled.

4. By using the thermographic camera installed in the search unit, it is possible to detect module (or cell) surface heating attributable to malfunction or failure.

5. By performing marking using the color marking ball launcher equipped with a laser pointer sighting device, a failure site can be instantaneously and clearly discriminated at the time of module (or cell) replacement work following failure site detection.

6. When the aerial vehicle nears an obstacle, an automatic flight location modification system incorporated in the aerial vehicle issues a warning sound and automatically modifies the flight path and flight angle, thereby enabling the aerial vehicle to avoid collision with the obstacle and fly safely.

7. If the aerial vehicle should fall into an unflyable condition owing to breakdown or the like, the emergency parachute and/or airbag is automatically activated to expand extensively, so that the solar power panel or other obstacle and the aerial vehicle itself, including equipment etc. installed therein, can be protected against harm and damage minimized.

BRIEF DESCRIPTION OF THE DRAWING

FIG. 1 is a block diagram of a solar power panel failure search and detect system according to the present invention.

BEST MODE FOR WORKING THE INVENTION

The solar power panel failure search and detect system according to the present invention is explained in detail below based on an embodiment shown in the drawing.

The solar power panel failure search and detect system according to the present invention comprises an aerial vehicle 10, a control unit 20, a search unit 30, and transmitter 40 for transmitting search result data and the like, and is configured with the search unit 30 and the transmitter 40 installed in the aerial vehicle 10.

FIG. 1 is a block diagram of a solar power panel failure search and detect system according to the present invention, which is constituted as a system that controls fly and search functions of the remotely located aerial vehicle 10 by means of the ground-based control unit 20.

In addition to being equipped with a main unit flight mechanism, the aerial vehicle 10 is further equipped with a flight control mechanism 12, incorporates the on-board search unit 30, and is concomitantly provided with the search result data transmitter 40, whereby it can be remotely controlled to glide or hover. Although failure- or degradation-induced hot spots can be detected and aerially photographed even during gliding only, preferably, in order to accurately discover malfunctions/failures and ensure clear search results (thermographic images), the aerial vehicle 10 should best be an unmanned rotorcraft, such as a helicopter, capable of hovering in addition to vertical and lateral maneuvering.

The flight control mechanism 12 is an apparatus that controls the flight path and flight angle of the aerial vehicle in response to signals received from the ground-based control unit 20 and can be configured to incorporate an automatic flight location modification mechanism 212 and an automatic accident avoidance mechanism 312 as additional components. The flight control mechanism 12 is constituted as prior art flight control means that enables stable flight within the range of solar power panel searched, and suffices if capable of ensuring output of a level enabling installation of the search unit 30 and the transmitter 40.

The control unit 20, which is installed on the ground and comprises flight path/flight angle controller 22, search unit controller 24, search result data receiver 26 and measurement result analyzer/processor 28, is configured to control the airborne aerial vehicle 10 and search unit 30 from the ground by remote control and perform data analysis.

The flight path/flight angle controller 22 is a remote operation system of the aerial vehicle 10 built into the control unit 20. By using the flight control mechanism 12, the flight path and angle of the aerial vehicle 10 can be controlled manually (or automatically) based on inflight images taken by imaging device 37 explained later, while it is also possible to install a program including flight speed, range, angle, etc. of the aerial vehicle 10 in advance and fly it by automatic remote operation based thereon.

The search unit control means 24 is a system that controls an angle detection sensor 32, an angle adjuster 33, a detector 34 and the imaging device 37, all of which are installed in the search unit 30 explained below. A configuration is adopted whereby remote operation from the ground is performed based on flight position and flight angle so as to maintain the angle of the ultrasonic and/or laser beam of the detection means with respect to the solar panel at a fixed value suitable for searching. The configuration is one that additionally incorporates a launcher 135 for shooting color balls, and further, after aiming a laser pointer sighting device 135*a* at a hot spot, transmits an instruction signal to shoot a color marking ball bullet from the launcher 135. The search unit 30 can be manually controlled based on images and data or can perform automatic searching in accordance with instructions given beforehand.

The search result data receiver 26 is constituted of a prior art data communication device and is configured for ground-based, on-time reception of solar panel image data imaged by the thermographic camera or other such imaging device 37 and transmitted from the search result data transmitter 40 installed in the airborne aerial vehicle 10. Further, the search results received by the search result data receiver 26 can be displayed on a screen of measurement result analyzer.

The measurement result analysis analyzer/processor 28, which is an image analysis system built into the ground-based control unit 20, analyzes thermographic data of the solar panel modules (or cells) received by the search result data receiver 26 and determines from temperature change appearing in the images whether malfunction or failure is present. In an embodiment having an additional mechanism, when malfunction or failure is determined, marking with paint is performed by shooting a color ball bullet onto the site concerned from the launcher 135.

The search unit 30 comprises the angle detection sensor 32, angle adjuster 33 and camera or other imaging device 37. A configuration is adopted that controls equipment installed in the search unit from the ground by signals transmitted from the search unit controller 24 of the ground-based control unit. When a problem caused by degradation or failure occurs in the solar power panel, the search unit 30 recognizes the heat-up characteristic exhibited by the malfunction site on the module surface and/or cell surface and identifies the malfunction site by detecting temperature change with the thermographic camera.

The angle detection sensor 32 is a sensor that uses the ultrasonic and/or laser beam to detect angle between the module surface (or cell surface) and the detector 34, and uses the ultrasonic and/or laser beam emitted from the detection means during search for angle measurement so as to maintain a fixed angle between the module surface (or cell surface) and the detector 34. As the optimum angle for detecting heat generation amount varies somewhat depending on, inter alia, installation angle of the solar power panel concerned, equipment used and weather, a configuration is adopted whereby an optimum angle is suitably set and the angle detection sensor 32, automatically taking the flight angle of the aerial vehicle into account in accordance therewith, transmits to the angle adjuster 33 a signal for correcting the angle.

The angle adjuster 33 is one that adjusts (corrects) the angle of the detector 34 based on the command signal from the angle detection sensor 32, and is configured to perform control so as to maintain the angle to the module surface measured by the ultrasonic and/or laser beam emitted from the detector 34 at optimum value (e.g., 90°). The angle adjuster 33 suffices insofar as it is a mechanism capable of steplessly fine-tuning the angle of a servo motor or the like and can be replaced by another conventional technology.

The detector 34, which is a unit installed in the search unit 30 that emits an ultrasonic and/or laser beam, emits an ultrasonic and/or laser beam onto a module (or cell) of the solar panel, thereby detecting hot spots that radiate heat owing to failure or the like. A detection signal (imaging signal) is sent to the camera or other imaging device 37 to collect image data of any malfunction site identified by the detector 34.

The camera or other imaging device 37, which comprises a thermographic camera built into the search unit, takes photographs of hot spots of the modules (or cells) of the solar panel in accordance with the detection results of the detector 34.

The search result data transmitter 40, constituted as prior art data communication device, transmits image data of malfunction or failure sites of the solar panel imaged by the thermographic camera or other imaging device 37 to the search result data receiver 26 built into the ground-based control unit.

The color ball launcher 135 installed in another embodiment of the present invention is a mechanism for shooting bullets charged with paint, which is adapted to perform marking by shooting color ball bullets to hit hot spots of solar power panel modules (or cells) detected by the detector 34. The color ball launcher 135, which incorporates the laser pointer sighting device 135*a*, can accurately indicate the location of malfunctioning modules (or cells) by performing accurate pinpoint marking of hot spots using the laser pointer sighting device 135*a*. In addition, the accurate marking with color balls also makes it possible to specify precisely at what location within an identified module (or cell) malfunctioning occurred.

Moreover, in another embodiment, the automatic flight location modification mechanism 212 comprises an obstacle detection unit 212*a* and a warning sound generator 212*b*, and the obstacle detection unit 212*a* comprises ultrasonic and/or laser beam sensors provided at multiple places on the aerial vehicle 10, whereby the aerial vehicle can navigate safely by continuously measuring distance between surrounding obstacles and the aerial vehicle 10 while flying. When the aerial vehicle 10 approaches an obstacle (solar panel included) closer than a predefined obstacle proximity distance, the flight location of the aerial vehicle 10 is automatically modified taking priority over any command signal from the ground-based flight path/flight angle controller. As a result, accidents involving collision of the aerial vehicle 10 with a solar power panel can be avoided, and damage to unexpected obstacles and the aerial vehicle 10 itself can also be avoided. The obstacle proximity distance can be suitably changed in line with the type of solar panel that is the subject of the search, its installation site and other such factors.

In still another embodiment, the automatic accident avoidance mechanism 312 comprises a parachute and/or airbag 312*a* and an automatic activation mechanism 312*b*, and a configuration is adopted by which, when the aerial vehicle 10 has become unflyable owing to an accident, failure or the like, the automatic activation mechanism 312*b* automatically activates and/or deploys the parachute and/or airbag 312*a* installed in the aerial vehicle 10 even in the absence of a command signal from the control unit. Owing to the provision of the automatic accident avoidance mechanism 312, even in a case where the aerial vehicle 10 loses its ability to fly and falls onto a solar panel, it lands on the solar panel either at very low speed or in a state capable of absorbing impact, so that the solar panel can be protected against damage.

Owing to the aforesaid configuration, the angle adjustment by the flight angle control mechanism of the aerial vehicle 10 and the angle detection sensor 32 of the search unit 30 makes it possible to maintain the angle of the ultrasonic and/or laser beam emitted from the detector 34 at a fixed angle nearly perpendicular to the solar panel. Although optimum angle during search depends on the type of solar panel and the inspection method, a measurement angle (irradiation angle of the ultrasonic and/or laser beam) nearly perpendicular to the solar panel surface is generally best for obtaining accurate search results. The present invention enables search/detection while maintaining such a measurement angle and in addition makes it possible to perform appropriate and accurate search/detect using command signals from the ground, without, as in the past, deploying many workers and installing much equipment.

Further, although the solar power panel failure search and detect system according to the present invention was developed for detecting solar panel module and/or cell failure, it can also use the thermographic camera to inspect an entire solar power system, because the aerial vehicle 10 can fly at various angles and altitudes within different ranges while detecting hot spots with the search unit 30. By discovering hot spots resulting from malfunction or failure also in connectors, storage batteries and other peripheral equipment and implementing management and maintenance, failure of the overall solar power system can be precluded to ensure safe and efficient use of renewable energy over the long term.

EXPLANATION OF SYMBOLS

10 Aerial vehicle
12 Flight control mechanism
20 Control unit
22 Flight path/flight angle control means
24 Search unit controller
26 Search result data receiver
28 Measurement result analyzer
30 Search unit
32 Angle detection sensor
33 Angle adjuster
34 Detector
37 Imaging device
40 Search result data transmitter
135 Color ball launcher
135*a* Laser pointer sighting device
212 Automatic flight location modification mechanism
212*a* Obstacle detection unit
212*b* Warning sound generator
312 Automatic accident avoidance mechanism
312*a* Parachute and/or airbag
312*b* Automatic activation mechanism

The invention claimed is:

1. A solar power panel failure search and detect system to detect malfunctioning or failed sites of a solar power panel using a search unit installed in a remotely controllable aerial vehicle, comprising;
   an aerial vehicle equipped with an on-board search unit and a flight controller to effect at least one of aerial gliding and hovering flight by a remote control;
   a ground-based control unit equipped with a flight/angle controller to control an aerial vehicle course and a flight angle, a search unit controller to control and regulate an angle sensor installed in the aerial vehicle, a receiver to receive search result data, and a processor to analytically process measurement results;
   a search unit equipped with the angle sensor to detect an angle between a detector and at least one of a module surface and a cell surface of a solar power panel, an angle adjuster to vary an angle of at least one of the detector and the aerial vehicle to maintain the detector at a fixed angle to said at least one of the module surface and cell surface of the solar power panel during a search, the detector detects and measures an amount of heat generated by at least one of a module and a cell of the solar power panel, and an imaging device comprising a camera to image a condition of the solar power panel; and
   a transmitter to transmit search result data comprising measurement and detection values and image data to the ground-based control unit.

2. The solar power panel failure search and detect system of claim 1, wherein the search unit detects and measures the amount of heat generated by modules and cells of the solar power panel individually using at least one of an ultrasonic and laser beam.

3. The solar power panel failure search and detect system of claim 1, wherein the search unit performs a search while maintaining an optimum search condition by using at least one of an ultrasonic and laser beam to measure a distance to said at least one of the module surface and the cell surface of the solar power panel and to measure and angle to said at least one of the module surface and the cell surface of the solar power panel.

4. The solar power panel failure search and detect system of claim 1, wherein the camera is a thermographic camera.

5. The solar power panel failure search and detect system of claim 1, wherein the search unit is equipped with a launcher, the launcher is configured to irradiate a spot on the solar power panel with a laser pointer based on analysis results of the control unit and to shoot a color marking ball to pinpoint a location of a malfunctioning or failed module or cell of the solar power panel.

6. The solar power panel failure search and detect system of claim 1, wherein the aerial vehicle is equipped with an obstacle detector, the obstacle detector comprises at least one of ultrasonic sensors and lasers at multiple locations, and the obstacle detector produces a warning sound and automatically modifies a flight location in response to a determination that the aerial vehicle is approaching an obstacle inclusive of a solar power panel that is closer than a predetermined distance.

7. The solar power panel failure search and detect system of claim 1, wherein the aerial vehicle is equipped with an automatic accident avoidance mechanism to automatically activate or deploy at least one of an emergency parachute and an airbag in response to an unflyable situation for the aerial vehicle to protect the solar power panel and the aerial vehicle from a crash impact due to a failure of the flight controller.

* * * * *